(12) United States Patent
Hofbauer et al.

(10) Patent No.: US 9,670,896 B2
(45) Date of Patent: Jun. 6, 2017

(54) DYNAMOELECTRIC CONVERTER AND MEDICAL OR DENTAL DEVICE HAVING A DYNAMOELECTRIC CONVERTER

(71) Applicant: W&H Dentalwerk Bürmoos GmbH, Bürmoos (AT)

(72) Inventors: Manfred Hofbauer, Oberndorf (AT); Karl Schmiedlechner, Ostermiething (AT); Walter Schuh, Buermoos (AT); Thomas Schmitzberger, Hochburg-Ach (AT)

(73) Assignee: W&H Dentalwerk Bürmoos GmbH, Bürmoos GmbH (AT)

( * ) Notice: Subject to any disclaimer, the term of this patent is extended or adjusted under 35 U.S.C. 154(b) by 522 days.

(21) Appl. No.: 14/199,910

(22) Filed: Mar. 6, 2014

(65) Prior Publication Data
US 2014/0255871 A1    Sep. 11, 2014

(30) Foreign Application Priority Data

Mar. 7, 2013 (EP) .................................. 13158142

(51) Int. Cl.
*A61C 1/05*       (2006.01)
*F03B 13/04*   (2006.01)
(Continued)

(52) U.S. Cl.
CPC .............. *F03B 13/04* (2013.01); *A61B 17/00* (2013.01); *A61C 1/05* (2013.01); *A61C 1/052* (2013.01);
(Continued)

(58) Field of Classification Search
CPC . F03B 13/04; A61B 2017/00553; A61C 1/05; A61C 1/052; H02K 5/128; H02K 7/1823; H02K 21/12; H02K 7/145

USPC .......................................................... 433/132
See application file for complete search history.

(56) References Cited

U.S. PATENT DOCUMENTS

2008/0261172 A1   10/2008   Rauchenzauner et al.
2009/0011380 A1    1/2009   Wang
(Continued)

FOREIGN PATENT DOCUMENTS

CN    201593450 U    9/2010
FR    2523891        9/1983
(Continued)

OTHER PUBLICATIONS

European Search Report for European Patent Application No. 13158142 (mailed Sep. 12, 2013).
(Continued)

*Primary Examiner* — Pedro Philogene
*Assistant Examiner* — David C Comstock
(74) *Attorney, Agent, or Firm* — Klarquist Sparkman, LLP

(57) ABSTRACT

Fluid-operated dynamoelectric converters for medical or dental devices are described. The dynamoelectric converters have: a fluid line which is designed in one piece with an outer sleeve of the dynamoelectric converter and protrudes at its end which faces away from the dynamoelectric converter beyond a connecting end of the medical or dental device; a fluid-operated impeller which is designed in one piece with a rotor sleeve receiving the magnetic element; a one-piece, sleeve-shaped magnetic return element which surrounds the rotor and the electric winding of the stator and has a magnetically conductive material.

20 Claims, 3 Drawing Sheets

(51) Int. Cl.
  *A61B 17/00* (2006.01)
  *H02K 5/128* (2006.01)
  *H02K 7/18* (2006.01)
  *H02K 21/12* (2006.01)
  *H02K 7/14* (2006.01)

(52) U.S. Cl.
  CPC ............ *H02K 5/128* (2013.01); *H02K 7/1823* (2013.01); *A61B 2017/00553* (2013.01); *H02K 7/145* (2013.01); *H02K 21/12* (2013.01)

(56) References Cited

U.S. PATENT DOCUMENTS

| | | | |
|---|---|---|---|
| 2010/0055642 A1* | 3/2010 | Rothenwaender | A61C 1/05 433/99 |
| 2012/0111590 A1* | 5/2012 | Rothenwaender | A61C 1/003 173/15 |
| 2012/0115101 A1 | 5/2012 | Rauchenzauner et al. | |

FOREIGN PATENT DOCUMENTS

| | | |
|---|---|---|
| JP | H0419958 | 5/1992 |
| JP | 2005341658 | 12/2005 |
| JP | 2011-101580 | 5/2011 |
| WO | WO2011/043143 | 4/2011 |

OTHER PUBLICATIONS

Office Action for Chinese Application No. 201410080334.4 (mailed May 25, 2016).

\* cited by examiner

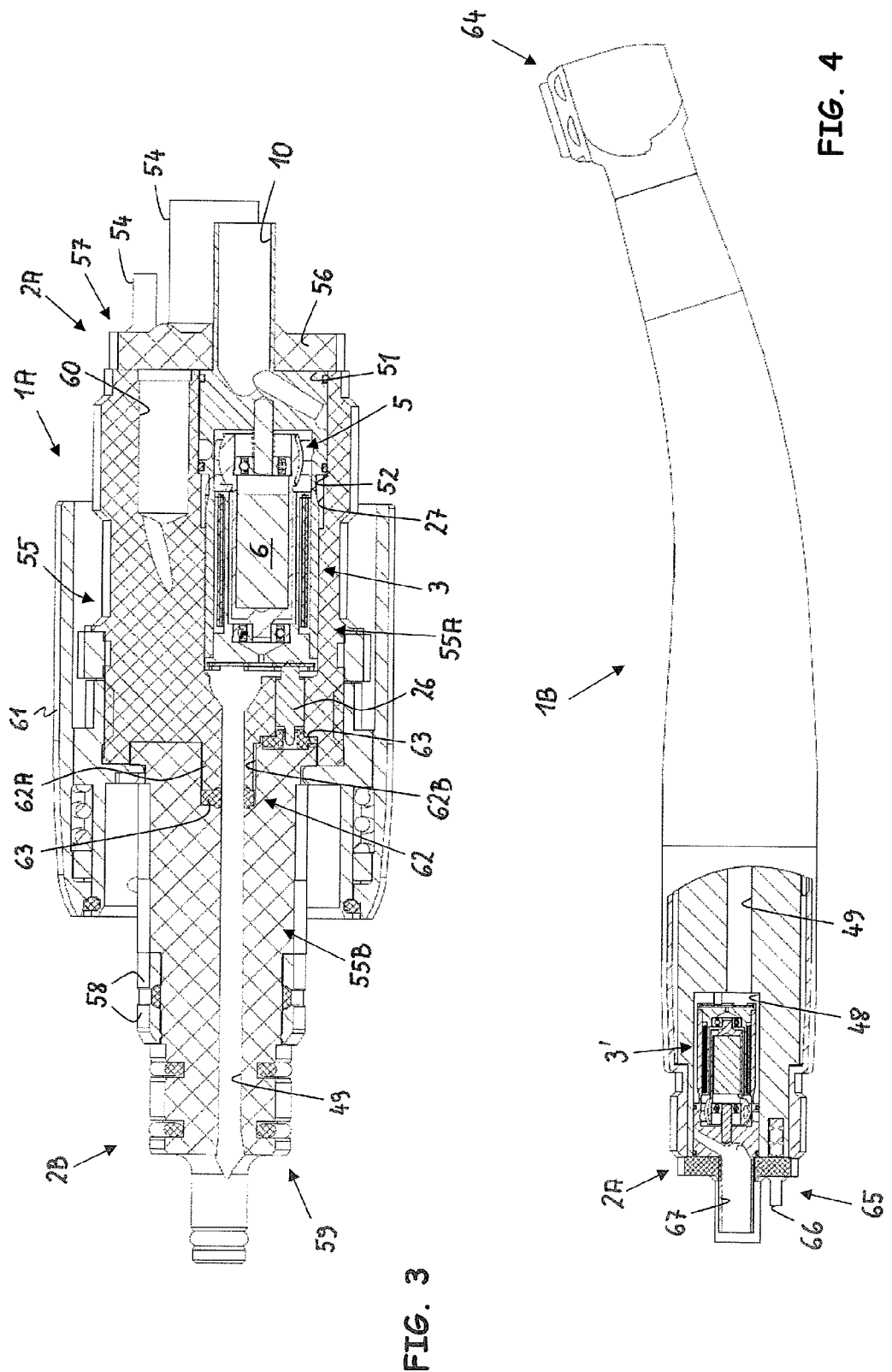

DYNAMOELECTRIC CONVERTER AND MEDICAL OR DENTAL DEVICE HAVING A DYNAMOELECTRIC CONVERTER

CROSS REFERENCE TO RELATED APPLICATION

The present application claims priority from pending European Patent Application No. 13158142.3, filed Mar. 7, 2013, which is incorporated herein by reference.

BACKGROUND

Field

The present application relates to a fluid-operated dynamoelectric converter for generating electricity and a medical, in particular dental, device having a fluid-operated dynamoelectric converter.

Description of Prior Art

US Patent Application US 2008/261172 A1 discloses a fluid-operated dynamoelectric converter for generating electricity and a medical, in particular dental, device in the form of a handpiece or a coupling element with a fluid-operated dynamoelectric converter. Providing a fluid-operated dynamoelectric converter in a handpiece or in a coupling element makes it possible to supply electricity from the dynamo converter to an electric load in the handpiece or in the coupling element, in particular to a lighting device, without connecting the handpiece or the coupling element to an electric energy source. Such handpieces or coupling elements that have fluid-operated dynamoelectric converters have been created and distributed by the applicant for several years and are very highly praised by the users.

Summary

It is thus an object of the present invention is to further develop a fluid-operated dynamoelectric converter for a medical or dental device. In particular the design of the fluid-operated dynamoelectric converter shall be simplified, its dimensions reduced and the integration into or installation in the medical, in particular dental, device should be facilitated without any sacrifices in terms of the electric power of the dynamoelectric converter.

This is achieved by embodiments of medical, in particular dental, devices and/or dynamoelectric converters (which are also referred to below as generators) which are described below.

According to one embodiment, a medical, in particular dental, device is provided having a connecting end that can be detachably connected to a fluid source and a fluid-operated dynamoelectric converter, wherein the fluid-operated dynamoelectric converter comprises: a rotor unit having a rotor that can be made to rotate by a fluid and at least one magnetic element, which is connected to the rotor, so that the magnetic element can also be made to rotate by the rotor which can be made to rotate, a stator having an electric winding which cooperates with the magnetic element that can be made to rotate in such a way that electricity can be generated in the electric winding, a sleeve, which surrounds at least parts of the rotor and/or of the stator and a fluid line, which is designed in one piece with the sleeve of the dynamoelectric converter and which protrudes at least at its end facing away from the dynamoelectric converter beyond the connecting end of the medical, in particular dental, device.

According to another embodiment, a fluid-operated dynamoelectric converter is provided, comprising: a rotor unit having an impeller which can be made to rotate by a fluid and which has a plurality of blades, at least one magnetic element, which is connected to the impeller, so that the magnetic element can also be made to rotate by the impeller being made to rotate, and having a rotor sleeve in which the at least one magnetic element of the rotor is situated, and a stator having an electric winding, which cooperates with the magnetic element that can be made to rotate such that electricity can be generated in the electric winding, wherein the impeller, in particular the blades of the impeller is/are designed in one piece with the rotor sleeve and is/are disposed on the outside of the rotor sleeve and/or at an end of the rotor sleeve in particular.

According to another embodiment, a fluid-operated dynamoelectric converter is provided, comprising: a rotor unit having an impeller that can be made to rotate by a fluid and at least one magnetic element that is connected to the impeller, so that the magnetic element can also be made to rotate by the impeller which is made to rotate, and a stator with an electric winding which cooperates with the magnetic element that can be made to rotate such that electricity can be generated in the electric winding, and a magnetic return element for concentrating and deflecting the magnetic field lines of the at least one magnetic element through the electric winding. The magnetic return element comprises a one-piece, sleeve-shaped magnetic return element, which surrounds the rotor and the electric winding and comprises a magnetically conductive material or it is designed as same.

In the embodiments mentioned above, the one-piece design of components produces a simpler integration of the fluid-operated dynamoelectric converter into the medical, in particular dental, device and/or requiring less space in the interior of the medical, in particular dental, device. Because of the smaller amount of space being used, it is thus additionally advantageously possible to guide other parts of the medical, in particular dental, device, for example, a fluid line or an optical conductor past the generator and/or to place them next to the generator. A substantial reduction in the size of the generator can be achieved in particular by combining a plurality of these one-piece designs.

By providing the fluid line which is designed in one piece with the sleeve of the generator and which protrudes beyond the connecting end of the medical, in particular dental, device at least at its end facing away from the generator, easy installation in the medical, in particular dental, device or a simple replacement of the generator is advantageously possible. The generator with the fluid line designed in one piece with the sleeve can preferably be inserted into a receptacle of the medical, in particular dental, device by displacement or plugging it in. In particular the receptacle is disposed or dimensioned so, that when the dynamoelectric converter is accommodated in the receptacle and has assumed its operating position, the fluid line, which is designed in one piece with the sleeve of the dynamoelectric converter protrudes beyond the connecting end of the medical, in particular dental, device at least at its end facing away from the dynamoelectric converter. The fluid line designed in one piece with the sleeve, in particular the end of the fluid line protruding beyond the connecting end thus preferably forms at least a part of a coupling device for connection to a fluid source and/or a coupling element for connection to a fluid source, in particular a coupling element that can be coupled detachably directly to a mating coupling element, for example, to a coupling section of a fluid line, in particular by plugging them together.

Further miniaturization of the fluid-operated dynamoelectric converter has preferably been achieved by the fact that the electric winding of the stator has a printed conductor. In particular the electric winding of the stator has a flexible or elastic or spirally rollable carrier element, in particular a flexible or spirally rollable circuit board. The carrier element is preferably designed planar or as a strip having two sides essentially opposite one another. The electric conductor of the electric winding, for example, a copper-containing electric conductor, is preferably provided on both sides of the carrier element which are essentially opposite one another. A through-contacting of the carrier element is provided in particular for connection of the electric conductor on both sides of the carrier element. Alternatively, it is of course also possible to provide the electric conductor of the electric winding on only one side of the carrier element.

A further simplification of the design and also a reduction in the size of the generator were preferably created by the fact that essentially only the sleeve, which surrounds at least parts of the rotor and/or stator and/or the outer sleeve and/or the outer sleeve having the one-piece, sleeve-shaped magnetic return element is/are provided for conducting the fluid driving the impeller. Thus, advantageously the provision of further guide elements for the fluid can be omitted. At least one of the following elements is provided for conducting the fluid on the sleeve or the outer sleeve, for example: a borehole, which is connected in particular to the fluid line that is designed in one piece with the sleeve or outer sleeve; a first outlet opening, which is provided on the outside of the sleeve or the outer sleeve and which in particular is connected to the borehole and/or to the fluid line, which is designed in one piece with the sleeve or the outer sleeve, so that the fluid can be conducted to the outside of the sleeve or the outer sleeve; at least one, preferably annular or arcuate, groove, which is formed on the outside of the sleeve or the outer sleeve and which is connected in particular to the fluid line that is designed in one piece with the sleeve or the outer sleeve and/or connected to the borehole and/or to the first outlet opening; at least one inlet opening, which is provided on the outside of the sleeve or the outer sleeve, so that fluid can be conducted from the outside of the sleeve or the outer sleeve, in particular from the groove into the interior of the sleeve or the outer sleeve, in particular to the impeller; a second outlet opening, which is provided on the outside of the sleeve or the outer sleeve and is designed to conduct the fluid to the outside of the sleeve after passage of the impeller. The generator and/or the medical, in particular dental, device is/are preferably designed so that the fluid after having passed the impeller can be conducted along the outside of the sleeve or the outer sleeve of the generator for cooling and/or in a recess adjacent the generator or surrounding it and/or can be discharged in particular in a fluid line connected to the generator.

According to another embodiment, a bearing surface and/or a bearing, in particular a roller bearing or ball bearing for rotatable mounting of the rotor sleeve and/or the impeller is/are disposed in the interior of a rotor sleeve, which accommodates the at least one magnetic element and/or in the interior of the impeller, in particular radially on the inside of the blades of the impeller. This causes a shortening, in particular an axial shortening and an even more compact design of the generator. A rotor shaft, which is accommodated in the interior of the rotor sleeve and/or in the interior of the impeller, in particular radially inside the blades of the impeller, is also provided for rotatable mounting of the rotor sleeve.

According to another embodiment, the rotor sleeve, which is designed in one piece with the impeller has a first section in which at least a portion of the at least one magnetic element is accommodated and has a second section on which the blades of the impeller are provided, wherein the outside diameter of the first section is smaller than the outside diameter of the second section, forming a setback on the first section. At least a portion of the electric winding and/or at least a portion of a carrier element or of a bearing element for the electric winding and/or an air gap of the generator is/are preferably provided in or on the setback. Through this embodiment, the compactness of the generator is also increased and its dimensions, in particular its diameter, is/are reduced.

It is pointed out explicitly that a combination of two or more of the embodiments described above is not only possible but this also makes it possible to achieve special advantages, in particular an additional miniaturization of the fluid-operated, dynamoelectric converter.

The medical, in particular dental, device, in which the fluid-operated dynamoelectric converter is provided comprises, for example, a straight, curved or pistol-shaped handpiece or handle element, an adapter or a coupling device. The handpiece or handle element, the adapter or the coupling device comprises, for example, an electric load, preferably a lighting device, in particular at least one optical semiconductor element, which can be supplied and/or can be operated with electricity generated by the generator. The generator and the electric load are preferably detachable from one another, in particular they are not disposed in the same part. The handpiece or the handle element, the adapter or the coupling device preferably include electric contacts and/or electric conductors which connect the generator to the electric consumer. The handpiece or the handle element comprises in particular at least one fluid-operated drive element for inducing movement to a tool that can be connected to the handpiece or the handle element. The adapter or the coupling device includes in particular a first connecting end that can be connected to a fluid source and a second connecting end at a distance from the first connecting end for releasable connection to a medical, in particular dental, instrument, for example, a handle element.

These and other embodiments will be described below with reference to the following drawings.

BRIEF DESCRIPTION OF THE DRAWINGS

FIG. 3 shows a longitudinal section through a medical, in particular dental, device in the form of a coupling device or an adapter with the fluid-operated dynamoelectric converter from FIGS. 1 and 2.

FIG. 4 shows a medical, in particular dental, device in the form of a handpiece with the fluid-operated dynamoelectric converter.

DETAILED DESCRIPTION

Figure 1:
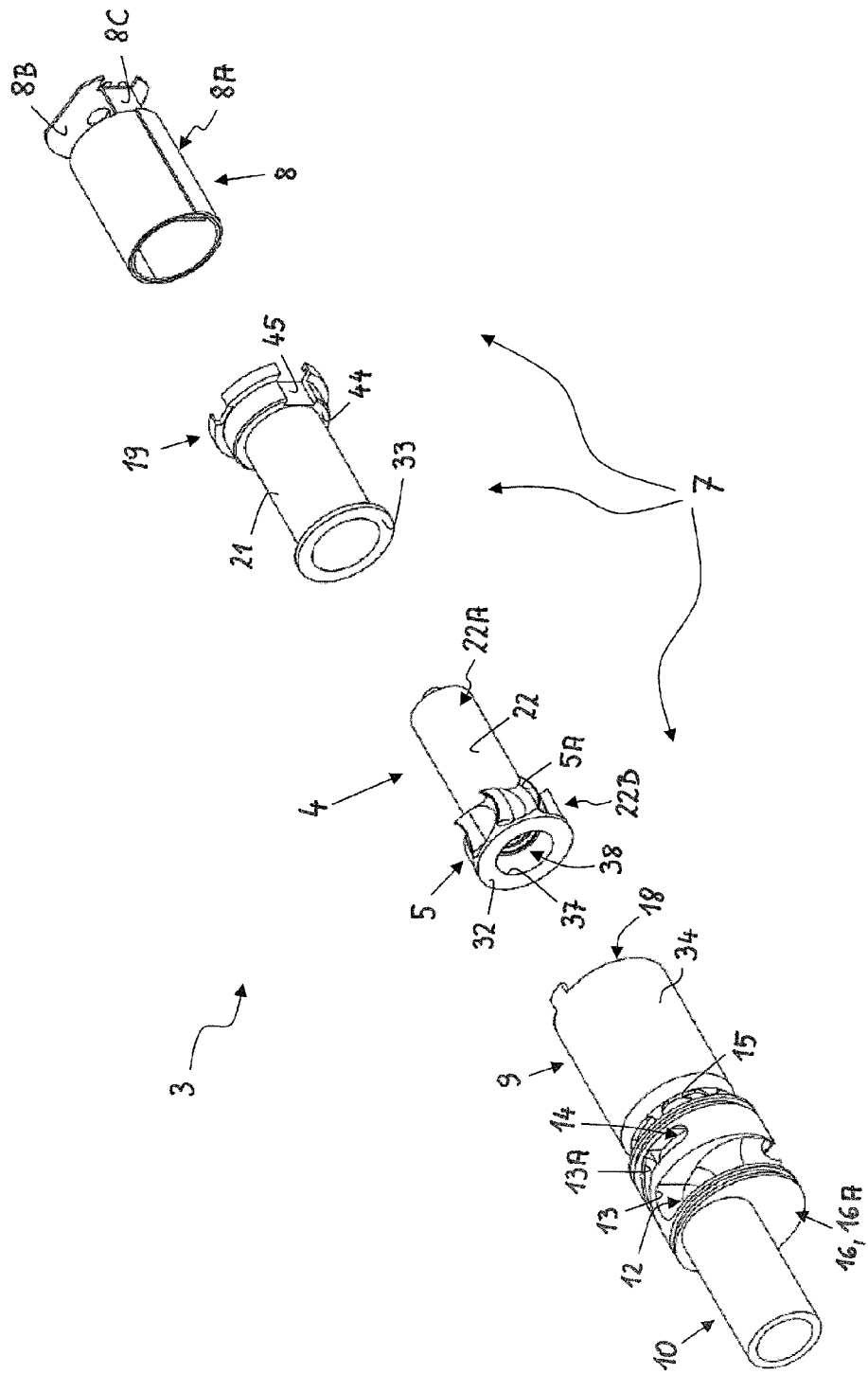
FIG. 1 shows an exploded diagram of an embodiment of a fluid-operated dynamoelectric converter.

FIG. 1 shows a rotor 4 and a stator 7 as the main elements of the fluid-operated dynamoelectric converter 3. The rotor 4 comprises an impeller 5 that can be set in rotation by fluid and at least one magnetic element 6. The magnetic element 6 is connected to the impeller 5, so that the magnetic element 6 can also be set in rotation by the impeller 5 which can be set in rotation. The stator 7 has an electric winding 8 which cooperates with the magnetic element 6 that can be set in rotation in such a way that electricity can be generated in the electric winding 8.

Figure 2:
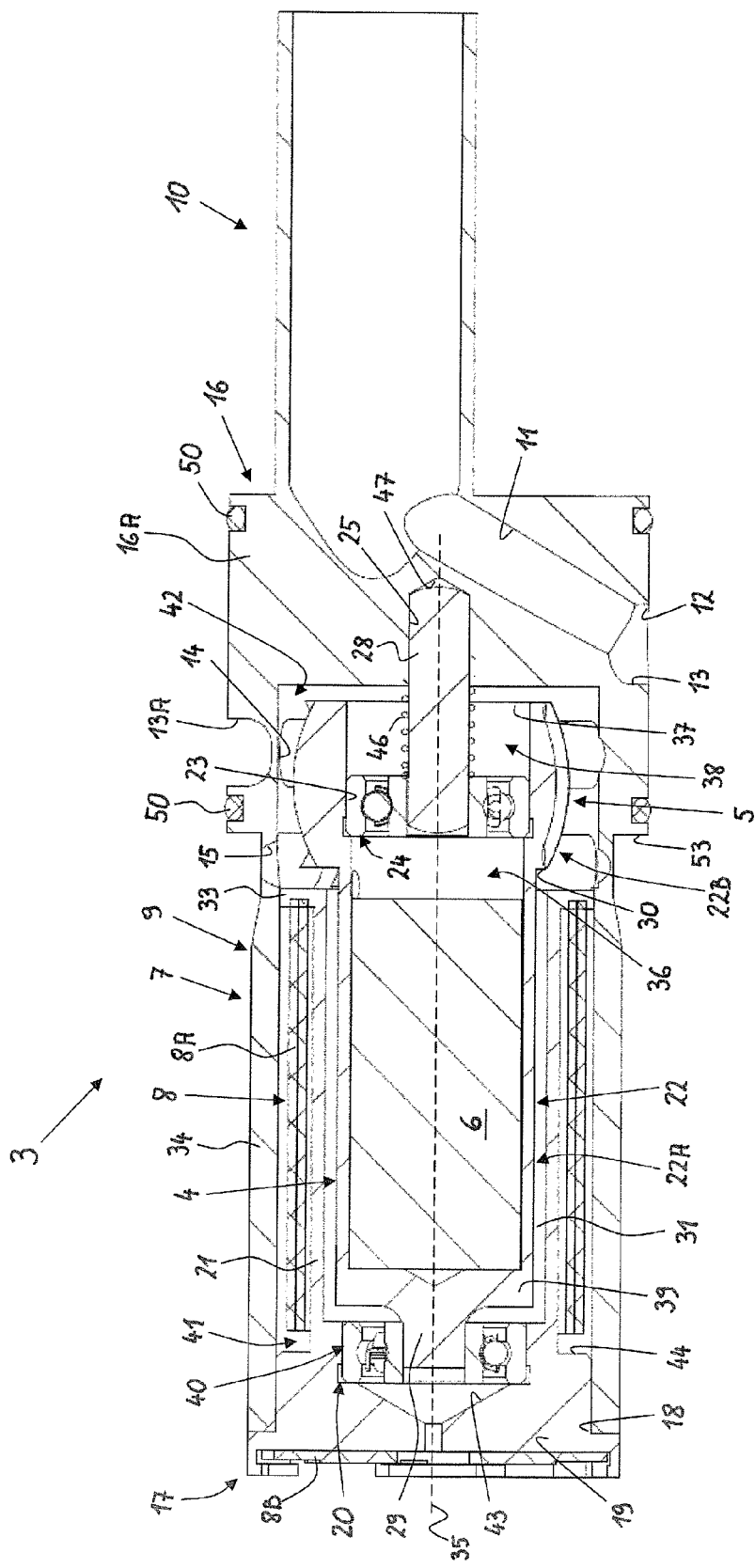
FIG. 2 shows a longitudinal section through the fluid-operated dynamoelectric converter from FIG. 1.

The fluid-operated dynamoelectric converter 3 (generator) is described in detail below with reference to FIGS. 1 and 2.

The rotor 4 comprises a longitudinal axis or axis of rotation 35 about which the rotor 4 is disposed rotatably. The magnetic element 6 of the rotor 4 is preferably designed as a permanent magnet. The magnetic element 6 is designed as a two-pole or multi-pole magnetic element. The magnetic element 6 is preferably cylindrical in shape.

The magnetic element 6 is preferably disposed or accommodated in a rotor sleeve 22 and/or secured therein, in particular being glued or pressed. The rotor sleeve 22 is preferably designed to be hollow and in particular has an interior space 36. At least the magnetic element 6 is preferably accommodated in the interior space 36. The rotor sleeve 22, in particular the interior space 36, is preferably cylindrical and/or elongated in shape. One end of the rotor sleeve 22 is preferably closed by an end wall 39.

The impeller 5 of the rotor 4, which can be driven by fluid, preferably has a plurality of blades 5A. The impeller 5 is preferably disposed essentially concentrically with the magnetic element 6 and/or with the rotor sleeve 22. The impeller 5, in particular the blades 5A, is/are preferably disposed radially around the axis of rotation 35. The impeller 5 is preferably hollow in design and/or has a cavity 38. The impeller 5, in particular the cavity 38, is especially preferably designed to receive at least one part of the generator 3, for example, to receive a bearing 24 for rotatable bearing support of the impeller 5 and/or to accommodate a shaft or a rotor shaft 28 for rotatable bearing of the impeller 5. A bearing surface 23 is preferably provided in the impeller 5, in particular in the cavity 38, in particular for the bearing 24 for rotatable bearing support of the impeller 5. The bearing 24 preferably comprises a roller bearing or ball bearing. The blades 5A of the impeller 5 are preferably disposed radially around the cavity 38. The cavity 38 preferably has an inside wall from which the blades 5A extend radially outward.

An annular flange 32 is preferably provided on at least one end of the impeller 5 which runs around the impeller 5 on its outside circumference. The blades 5A of the impeller 5 preferably follow the annular flange 32 or they are connected to the annular flange 32. The annular flange 32 preferably forms an axial end of the impeller 5. The annular flange 32 is preferably provided to guide the fluid which drives the impeller 5 or which acts upon the impeller 5. The annular flange 32 is preferably designed in one piece with the impeller 5 and/or the blades 5A.

The impeller 5, in particular the blades 5A of the impeller 5, is/are especially preferably designed in one piece with the rotor sleeve 22. The impeller 5, in particular the blades 5A, is/are especially preferably provided on the rotor sleeve 22. The blades 5A of the impeller 5 are disposed on the outside of the rotor sleeve 22 and/or on one end of the rotor sleeve 22 in particular. The impeller 5, in particular the blades 5A and the rotor sleeve 22 are in particular thus designed as a single combined part. The interior space 36 of the rotor sleeve 22 and the cavity 38 of the impeller are preferably connected to one another or together form a combined interior space.

The interior space 36 of the rotor sleeve 22 or the joint interior space, which is formed by the interior space 36 and the cavity 38 is preferably designed to receive a bearing 24 for rotatable support of the impeller 5 and of the rotor sleeve 22 with the magnetic element 6 and/or to receive a rotor shaft 28 for rotatable support of the impeller 5 and the rotor sleeve 22 with the magnetic element 6. A bearing point or bearing surface 23, in particular for the bearing 24, is preferably provided in the interior space 36 or in the joint interior space. The bearing 24 preferably comprises a roller bearing or a ball bearing. The blades 5A of the impeller 5 are preferably disposed radially around the interior space 36 or the shared interior space. The joint interior space preferably has an inside wall from which the blades 5A extend radially outward.

An opening 37 through which at least the magnetic element 6, optionally an additional element of the generator 3, in particular the bearing 24 and/or the shaft 28 can be inserted into the rotor sleeve 22 and/or into the impeller 5, is preferably provided on the rotor sleeve 22, in particular on one end of the rotor sleeve 22 or on the impeller 5. The opening 37 is preferably disposed on the end of the rotor sleeve 22 and/or on the end of the impeller 5 opposite the end wall 39. The rotor sleeve 22 with the integrally designed impeller 5 is preferably designed as a sleeve, in particular a pot-shaped sleeve having a borehole 36, 38 in which the magnetic element 6 and in particular the bearing 24 and/or the shaft 28 is/are disposed.

A rotor journal 29, which is designed in one piece with the rotor sleeve 22 and/or with the end wall 39 in particular, is preferably provided for rotatable bearing support of the rotor sleeve 22 and/or of the impeller 5. The rotor journal 29 is preferably disposed on one end of the rotor sleeve 22, in particular on the end wall 39 of the rotor sleeve 22. A bearing 40, in particular a roller bearing or a ball bearing for rotatable bearing support of the rotor sleeve 22 and/or of the impeller 5 is preferably provided on the rotor journal 29.

The rotor sleeve 22 preferably comprises a first section 22A, in which at least a part of the at least one magnetic element 6 is accommodated, and a second section 22B on which the impeller 5 or the blades 5A of the impeller 5 are provided. The outside diameter of the first section 22A is smaller than the outside diameter of the second section 22B. Therefore, a setback 30 is formed on the first section 22A. The side wall or the axial border of the setback 30 is formed in particular by the blades 5A of the impeller 5, in particular by their lateral ends or free side ends. The impeller 5, in particular the blades 5A of the impeller 5 are arranged adjacently to the first section 22A. The outside diameter of the impeller 5 or of the blades 5A, at least of the outer or radial ends of the blades 5A is preferably larger than the outside diameter of the first section 22A.

At least a portion of the electric winding 8 and/or at least a part of a bearing or carrier element 21 for the electric winding 8 and/or part of an air gap 31 of the dynamoelectric converter 3 is preferably provided in or on the setback 30. The electric winding 8 and/or at least a part of the bearing or carrier element 21 and/or the air gap 31 is/are thus preferably disposed axially adjacent to the impeller 5, in particular to the blades 5A of the impeller 5. The electric winding 8 and/or at least a part of the bearing or carrier element 21 and/or the air gap 31 preferably extend(s) over essentially the entire first section 22A.

The electric winding 8 of the stator 7 is preferably disposed at least around a part of the rotor 4, in particular around the magnetic element 6 and/or the rotor sleeve 22, preferably its section 22A. The electric winding 8 comprises, for example, at least one wound coil winding. The electric winding 8 preferably comprises at least one printed conductor or printed circuit board 8A. In particular the electric winding 8 comprises a flexible or elastic carrier element or one that can be rolled up in a spiral, in particular a flexible circuit board or a circuit board that can be rolled up in a spiral, on which the printed conductor 8A is disposed. As shown by the sectional diagram in FIG. 2, the electric winding 8 preferably has 2-4 levels or layers disposed (radially) one above the other because of the spiral configuration of the carrier element that can be rolled up in a spiral form. The carrier element that can be rolled up in a spiral form is preferably provided with printed conductors 8A on both sides.

The electric winding 8 of the stator 7 is either disposed freely around the rotor 4 without any additional carrier or bearing element or a carrier or bearing element 21 is provided for the electric winding 8. The carrier or bearing element 21 is preferably designed to be cylindrical, in particular as a hollow cylinder or as a sleeve shape. The carrier or bearing element 21 preferably has an axial dimension that is approximately the same as or somewhat longer than that of the electric winding 8. The carrier or bearing element 21 preferably surrounds at least parts of the rotor 4 or receives at least parts of the rotor 4 in its interior, for example, the magnetic element 6 and/or the rotor sleeve 22. The carrier or bearing element 21 is separated in particular by the air gap 31 from the magnetic element 6 and/or the rotor sleeve 22.

The carrier or bearing element 21 preferably comprises at least one free end which in particular faces the impeller 5 or is arranged adjacently to the impeller 5, preferably to the blades 5A, but in particular at a distance from it. This free end preferably has an annular flange 33 which is disposed adjacently to the impeller 5, in particular on the blades 5A. The (radial) height of the annular flange 33 preferably corresponds approximately to the (radial) height of the electric winding 8. The carrier or bearing element 21 and the annular flange 33 preferably form a chamber 41 for the electric winding 8, in particular with additional parts of the generator 3, for example, with a closure element 19 and/or a sleeve 9. The chamber 41 is preferably designed so that it separates or encloses the electric winding 8 from additional parts of the generator 3, in particular protecting it from a direct exposure to the fluid driving the impeller 5.

The annular flange 33 is preferably also designed as a conducting element for the fluid driving the impeller 5. The annular flange 33 with the annular flange 32 in particular forms a conducting device for the fluid, for example, for conducting the fluid to the impeller 5 or away from the impeller 5. The two annular flanges 32, 33 preferably cooperate with additional elements of the generator 3 to accomplish this, for example, with the sleeve 9 and/or with an opening 12, 14, 15, a borehole 11 or a groove 13 of the generator 3 provided for conducting a fluid. The annular flange 33 is preferably provided in particular with additional elements of the generator 3, for example, the sleeve 9, to form a chamber 42 for the impeller 5. The annular flange 33 preferably separates the chamber 41 for the electric winding 8 from the chamber 42 for the impeller 5.

The carrier or bearing element 21 is preferably connected to a closure element 19, in particular being designed in one piece. The closure element 19 is provided in particular to close an opening 18 of the generator 3, for example, of an outer sleeve 9 of the generator 3, preferably closing it releasably. The closure element 19 is preferably designed to be inserted at least partially into the opening 18. The closure element 19 is preferably provided to form with at least one side or surface an outside wall or an outside surface of the generator 3. The closure element 19 is preferably provided on an end of the carrier or bearing element 21 and closes in particular one end of the carrier or bearing element 21. The closure element 19 preferably comprises at least one receptacle or borehole 43 to receive a part of the rotor 4, in particular the rotor sleeve 22 and/or the rotor journal 29 or of the bearing 40 for rotatable bearing support of the rotor sleeve 22 and/or of the impeller 5. The closure element 19, in particular the borehole 43, preferably comprises a bearing surface 20 for rotatable bearing support of the magnetic element 6 of the rotor 4 and/or of the impeller 5. The bearing 40 is in particular disposed on the bearing surface 20.

The outside diameter of the carrier or bearing element 21 is preferably smaller than the outside diameter of the closure element 19, so that a setback 44 is formed in particular. The closure element 19, in particular the setback 44, preferably borders the chamber 41. The electric winding 8 is preferably disposed between the setback 44 and the annular flange 33.

The dynamoelectric converter 3 preferably comprises a sleeve or an outer sleeve 9 which surrounds at least parts of the rotor 4 and/or of the stator 7, in particular at least the electric winding 8. The sleeve 9 preferably comprises at least one cylindrical section in which the at least one magnetic element 6 and/or the rotor sleeve 22 and/or the electric winding 8 is/are disposed in particular. The sleeve or the outer sleeve 9 is preferably designed in one piece and/or elongated. The sleeve 9 preferably surrounds the rotor 4 and the electric winding 8 of the stator 7 along its entire axial extent. The generator 3 is preferably designed as an exchangeable generator cartridge, wherein the outer sleeve 9 in particular forms the cartridge sleeve on which the parts of the generator 3 are supported and/or to which they are attached directly or indirectly.

The sleeve or outer sleeve 9 preferably comprises a receiving end 17 on which an opening 18 through which the rotor 4 and the electric winding 8 of the stator 7 can be inserted, is provided. The opening 18 is releasably closable, in particular by the closure element 19 described above. The sleeve or outer sleeve 9 and the closure element 19 thus preferably border a chamber in which the rotor 4 and the electric winding 8 can be or are accommodated.

The printed conductor 8A described above preferably comprises a section 8B, which is provided on the outside of the sleeve 9 of the dynamoelectric converter 3 and/or on the outside of the closure element 19, so that the section 8B is or can be connected, in particular to an electric contact 26 disposed outside of the sleeve 9 (see also FIG. 3). An opening and/or a pass-through 45 for the printed conductor 8A or the section 8B or a connecting section 8C of the printed conductor 8A is/are preferably provided for this purpose on the sleeve 9 and/or on the closure element 19. The passage 45 preferably connects the chamber 41 for the electric winding 8 to the outside of the sleeve 9 and/or of the closure element 19. The printed conductor 8A or the connecting section 8C preferably extends through the passage 45, so that the section 8B is connected to the part of the printed conductor 8A disposed in the interior of the sleeve 9.

The section 8B of the printed conductor 8A is preferably disposed essentially in parallel with the outside of the closure element 19. The section 8B of the printed conductor 8A is preferably disposed essentially at a right angle to the longitudinal axis 35 of the rotor 4 and/or essentially concentric with the rotor 4. At least one part of the closure element 19 is preferably disposed between the section 8B and the part of the printed conductor 8A disposed in the interior of the sleeve 9. The section 8B and/or the connecting section 8C of the printed conductor 8A are preferably designed to be essentially flat (in contrast with the spiral configuration of the remaining printed conductor 8A). Two exposed electric contacts are preferably provided on one side of the flat section 8B, in particular on the side facing away from the rotor 4.

The sleeve or outer sleeve 9 preferably comprises an connecting end 16, which is essentially opposite the receiving end 17 in particular. The connecting end 16 is formed in particular by a connecting end wall 16A and/or comprises an connecting end wall 16A. The connecting end 16 and/or the connecting end wall 16A is/are designed in particular in one piece with the sleeve or the outer sleeve 9. The sleeve or the outer sleeve 9 and the connecting end wall 16A thus preferably border a chamber, in particular jointly with the closure element 19 in which the rotor 4 and the electric winding 8 is or can be accommodated.

The rotor shaft 28 for a rotatable bearing support of the rotor 4 and/or of the impeller 5 is preferably supported in a bearing surface 25 provided outside of the rotor sleeve 22 and/or of the impeller 5, in particular in a wall of the sleeve 9. The bearing surface 25 for rotatable bearing support of the impeller 5 and/or of the rotor 4 is especially preferably provided in the connecting end wall 16A of the sleeve 9. The bearing surface 25 comprises in particular a borehole 47 in the connecting end wall 16A to receive at least a part of the rotor shaft 28. The rotor shaft 28 is preferably accommodated in a rotationally fixed manner in the connecting end wall 16A and/or in its borehole 47. A spring element 46, which prestresses the rotor 4, is preferably provided on the rotor shaft 28. The spring element 46 is preferably supported on the connecting end wall 16A.

At least one element, which is designed for conducting the fluid driving the impeller 5 is preferably provided in or on the sleeve or the outer sleeve 9. This conducting element comprises, for example, at least one of the elements described below:

- at least one inlet opening 14 which is designed to conduct a fluid for driving the impeller 5 from the outside of the sleeve or the outer sleeve 9 into the interior of the sleeve or outer sleeve 9, in particular to the impeller 5. The at least one inlet opening 14 is preferably disposed radially to the impeller 5. The at least one inlet opening 14 is preferably disposed so, that the impeller 5 can be acted upon by the fluid radially. The at least one inlet opening 14 preferably comprises a through-hole in the sleeve or outer sleeve 9. A plurality of inlet openings 14 which are disposed essentially at regular intervals, in particular at angle arcs to one another are preferably provided. The at least one inlet opening 14 is preferably connected in a fluid-conducting manner to the chamber 42 for the impeller 5. The sleeve or outer sleeve 9 is preferably designed or disposed in a medical or dental device 1A, 1B such that the fluid can be conducted along the outside of the sleeve or the outer sleeve 9, in particular to the at least one inlet opening 14. The generator 3 is preferably disposed in a receptacle 27, 48 of a medical or dental device 1A, 1B (see FIGS. 3 and 4) such that the fluid for driving the impeller 5 can be conducted in the receptacle 27, 48 or between a wall of the receptacle 27, 48 and the sleeve or outer sleeve 9 of the generator 3;
- at least one groove 13, preferably ring-shaped or arc- or C-shaped, provided on the outside of the outer sleeve 9, which is connected to the at least one inlet opening 14, so that a fluid for driving the impeller 5 can be conducted through the groove 13 to the inlet opening 14. A groove 13 which runs essentially parallel to the connecting end wall 16A on the connection side is preferably provided. At least one groove 13A branching off from the groove 13 is preferably provided, connecting the at least one inlet opening 14 to the arc-shaped groove 13. A branching groove 13A is preferably provided for each inlet opening 14. The at least one branching groove 13A preferably forms an angle to the connecting end wall 16A. Multiple branching grooves 13A which branch off essentially at regular intervals from the arc-shaped groove 13 are preferably provided;
- a fluid line 10 which is designed in one piece with the sleeve or the outer sleeve 9 and which protrudes beyond an end, in particular the connecting end 16 on the connection side, of the outer sleeve 9 and which is connected to the inlet opening 14 and/or the groove 13 in a fluid-conducting manner, so that a fluid flowing in the fluid line 10 can be conducted to the inlet opening 14 and/or the groove 13. The fluid line 10 which is designed in one piece with the sleeve or the outer sleeve 9 stands away from the sleeve or the outer sleeve 9 in particular. The fluid line 10 which is designed in one piece with the sleeve or the outer sleeve 9 is disposed in particular on an connecting end 16 or on an connecting end wall 16A of the sleeve or the outer sleeve 9. The fluid line 10 preferably has a tubular or hollow cylindrical shape. The fluid line 10 is preferably disposed eccentrically or offset to the longitudinal axis 35. The outside diameter of the fluid line 10 which is designed in one piece with the sleeve or the outer sleeve 9 is preferably smaller than the outside diameter of at least one section of the sleeve 9, in particular of the connecting end 16 or of the connecting end wall 16A on the connection side;
- at least one bore or borehole 11 in the sleeve or the outer sleeve 9 which connects the fluid line 10 which is designed in one piece with the sleeve or the outer sleeve 9 to the inlet opening 14 and/or the groove 13 in a fluid-conducting manner. The borehole 11 is preferably provided in the end wall 16A on the connection side. The inside diameter of the borehole 11 is preferably smaller than the inside diameter of the fluid line 10. The borehole 11 is preferably disposed at an angle to the fluid line 10 wherein the angle in particular amounts to less than 90°, especially preferably between approximately 45° and 85°. The borehole 11 preferably opens at one end into the fluid line 10. The borehole 11 preferably ends on the outside of the sleeve or the outer sleeve 9;
- a first outlet opening 12 which is provided in particular on the outside of the sleeve or the outer sleeve 9 and is connected to the borehole 11 and/or the fluid line 10, so that the fluid can be conducted to the outside of the sleeve or the outer sleeve 9 and/or in the groove 13 and/or to the inlet opening 14 and/or to the receptacle 27, 48 of the medical or dental device 1A, 1B. The first outlet opening 12 is preferably provided in or on the groove 13;
- at least one second outlet opening 15 which is designed to conduct the fluid to the outside of the outer sleeve 9 after passage of/through the impeller 5. The second outlet opening 15 is preferably connected to the chamber 42 for the impeller 5 in a fluid-conducting connection. The sleeve or outer sleeve 9 is preferably designed or disposed in a medical or dental device 1A, 1B so, that the fluid can be conducted on the outside of the sleeve or outer sleeve 9 after passage of the impeller 5, in particular being conducted in the direction of a fluid line 49 that is connected to the generator 3 and/or the receptacle 27, 48 (see FIGS. 3 and 4). The generator 3 is preferably disposed in the receptacle 27, 48 so, that the fluid can be conducted in the receptacle 27, 48 or between a wall of the receptacle 27, 48 and the sleeve or the outer sleeve 9 of the generator 3 after passage through the impeller 5. The at least one second outlet opening 15 is preferably disposed adjacently to the annular flange 33 and/or axially between the impeller 5 and the electric winding 8.

At least the borehole 11, the grooves 13, 13A and the openings 12, 14, 15 are preferably provided in a section of the sleeve or the outer sleeve 9, in particular in a section with the connecting end wall 16A on the connection side, which is disposed adjacently to a section 34 of the sleeve or the outer sleeve 9, which surrounds the magnetic element 6 and/or the electric winding 8. At least one sealing element 50 is preferably provided on the outside of the sleeve or the outer sleeve 9, separating, for example, at least two of the elements described above for conducting the fluid driving the impeller 5 from one another essentially in a fluid-tight manner, preferably separating the at least one second outlet opening 15 from at least one of the other elements 11, 12, 13, 13A, 14 in a fluid-tight manner. At least one sealing element 50, which seals the section of the outside of the sleeve or the outer sleeve 9 along which the fluid can be conducted, is preferably provided on the outside of the sleeve or the outer sleeve 9.

The generator preferably has a magnetic return element or yoke for concentrating and directing the magnetic field lines of the at least one magnetic element 6 through the electric winding 8. The yoke preferably comprises a one-piece, sleeve-shaped magnetic return element or yoke element 34, which surrounds the rotor 4 and the electric winding 8 and comprises a magnetically conductive material. The one-piece, sleeve-shaped magnetic yoke element 34 is especially preferably part of the, in particular one-piece, sleeve or outer sleeve 9 of the dynamoelectric converter 3. The one-piece, sleeve-shaped magnetic yoke element 34 is in particular connected in one piece to the sleeve or the outer sleeve 9 or is designed in one piece with the sleeve or the outer sleeve 9 and/or the one-piece, sleeve-shaped magnetic yoke element 34 is part of the cartridge sleeve of the generator 3. The one-piece, sleeve-shaped magnetic yoke element 34 is preferably made of steel. The one-piece, sleeve-shaped magnetic yoke element 34 preferably has a wall thickness of approximately 0.2 mm to approximately 1.0 mm, in particular from approximately 0.4 mm to approximately 0.5 mm.

According to the preceding description, the opening 18 through which the rotor 4 and the electric winding 8 of the stator 7 can be inserted is preferably provided on the one-piece, sleeve-shaped yoke element 34, in particular on its receiving end 17. Moreover the opening 18 on the one-piece, sleeve-shaped magnetic yoke element 34 may have the same features as those described above. In particular the opening 18 on the one-piece, sleeve-shaped magnetic yoke element 34 is releasably closable by the closure element 19. In addition, the section 8B of the printed conductor 8A may preferably be provided on the outside of the one-piece, sleeve-shaped magnetic yoke element 34, so that the section 8B can be connected to an electric contact 26 disposed outside of the outer sleeve 9.

The generator 3 preferably has an outside diameter of less than approximately 1 cm, in particular less than approximately 8 mm. The generator 3 not including the fluid line 10 (i.e., from the receiving end 17 to the connecting end 16 on the connection side) preferably has a length of less than approximately 2 cm, in particular of less than approximately 1.7 cm. A generator 3 is preferably designed to generate a power of approximately 0.05 watt to approximately 2 watts, in particular of approximately 0.1 watt. In particular the generator 3 is designed to supply electricity to a lighting device, in particular at least one optical semiconductor element (light-emitting diode).

FIG. 3 shows a first embodiment of a medical or dental device 1A with the fluid-operated dynamoelectric converter 3. The device 1A comprises an adapter or a coupling device 1A. The coupling device 1A in particular comprises a connecting end 2A that can be releasably connected to a fluid source and has a connecting end 2B at a distance from the former for releasable connection to a medical, in particular dental, instrument, for example, a handle element. The coupling device 1A is designed in particular as a rotary or swivel coupling which comprises a cylindrical or hollow cylindrical coupling journal 59 which can be inserted into a corresponding receptacle of a device that is connectable to the coupling device 1A, so that the coupling device 1A and the device that can be connected to it can be rotated relative to one another. The adapter or the coupling device 1A preferably comprises a body 55 and an outer sleeve 61 surrounding the body 55 at least partially.

The generator 3 is disposed in a receptacle 27 in the coupling device 1A. The receptacle 27 is preferably provided on one end of the coupling device 1A, in particular on the connecting end 2A. The receptacle 27 is preferably accessible from the end of the coupling device 1A at which the receptacle 27 is provided, in particular being accessible from the connecting end 2A, especially preferably by way of an opening 51 on the end or the connecting end 2A. The generator 3, in particular in the form of a replaceable generator cartridge, is preferably insertable into the receptacle 27 or exchangeable through the opening 51. At least one stop 52, for example, a setback or a ring shoulder that contacts a mating contact 53 on the generator 3 is preferably provided in the receptacle 27.

The dynamoelectric converter 3 is especially preferably disposed in the receptacle 27 so, that the fluid line 10 which is designed in one piece with the sleeve or the outer sleeve 9 protrudes at least at its end facing away from the dynamoelectric converter 3, beyond the connecting end 2A of the medical, in particular dental, device 1A, in particular the coupling device 1A. The fluid line 10 is thus releasably connectable directly to a fluid line in particular, preferably to a fluid line, which is in turn connected to a fluid source, for example, to a fluid line of a supply tubing. The fluid line 10 which is designed in one piece with the sleeve or the outer sleeve 9 thus preferably forms at least a part of a coupling unit 57 on the connecting end 2A for connection to a fluid source and/or a coupling element for connection to a fluid source. Optionally at least one additional line 54 is also provided on the coupling unit 57 for transfer of a fluid, in particular in the form of a tube protruding away from the connecting end 2A. This at least one additional line 54 is either designed in one piece with at least a part of the body 55 of the coupling device 1A or it is inserted into a receptacle of the body 55. A sealing element 56 in particular in the form of a rubber elastic sealing washer, which seals the opening 51 and the receptacle 27 in particular is provided on the connecting end 2A and/or on the coupling unit 57.

The receptacle 27 is preferably designed for conducting the fluid that drives the impeller 5. The receptacle 27 and the sleeve or the outer sleeve 9 of the generator 3 are in particular disposed such to form a gap or a distance between them, in which the fluid can flow, optionally the fluid flowing towards the impeller 5 and/or away from the impeller 5. A fluid line 49, which is designed for receiving the fluid that has passed the impeller 5, is arranged adjacently to the receptacle 27 or connected to the receptacle 27. The fluid line 49 is preferably connectable or connected to a fluid-operated drive device for a treatment tool and/or to an opening for discharging the fluid to the environment. To this end, the fluid line 49 is preferably connected to an opening on the connecting end 2B, in particular on the coupling journal 59, through which the fluid can be transferred to the fluid-operated drive device and/or to the discharge opening.

Accordingly, at least one additional line or borehole 60 extends from the at least one line 54 at the connecting end 2A through the adapter or the coupling device 1A, in particular up to the connecting end 2B and/or the coupling journal 59, so that a medium can be conducted therein and in particular can be transferred to an instrument that can be connected to the connecting end 2B. To do so, the at least one additional line 60 is preferably connected to an opening on the connecting end 2B, in particular on the coupling journal 59 by which the medium can be dispensed.

An electric contact 26 provided in the device 1A connects the generator 3 to an electric load. The electric load is optionally disposed in the adapter or in the coupling device 1A or in a device that can be connected to it, in particular by way of the connecting device 2B. The electric contact 26 preferably comprises a printed circuit. In particular the electric contact 26 comprises a flexible or elastic carrier element, in particular a flexible or elastic circuit board. The electric contact 26 is preferably connected to additional electric contacts 58 on the connecting end 2B, in particular on the coupling journal 59, so that the electricity generated by the generator 3 can be transferred to an instrument that can be connected to the connecting end 2B. The electric contacts 58 are designed, for example, as an electric contact ring and/or as part of a sliding contact.

According to a preferred embodiment, the adapter or the coupling device 1A has a body 55 and an outer sleeve 61 that can be attached to the body, wherein the body 55 comprises: a connecting end 2B on the instrument side and a connecting end 2A on the supply side, wherein a coupling journal 59 for releasable connection to a medical, in particular dental, instrument is provided on the connecting end 2B and a coupling unit 57 for releasable connection to a supply unit, control unit and/or regulating unit is provided on the connecting end 2A, and at least one line 26, 49, 60 for transferring a medium, energy and/or data, said line extending through the coupling device 1A or connecting the connecting end 2B and the connecting end 2A, so that a medium, energy and/or data can be transferred through the coupling device 1A, wherein the body 55 of the coupling device 1A comprises two sections 55A, 55B that can be releasably connected to one another and wherein the connecting end 2A is provided on the first section 55A and the connecting end 2B is provided on the second section 55B.

An interface or sectional plane is preferably disposed at an angle to the longitudinal axis of the coupling device 1A between the two sections 55A, 55B, in particular essentially at a right angle to the longitudinal axis of the coupling device 1A. The angle between the plane of intersection and the longitudinal axis of the coupling device 1A is in particular at least greater than 0°. The second section 55B is preferably formed essentially by the coupling journal 59.

The first and second sections 55A, 55B are preferably connectable to one another through a plug connection 62, which comprises a plug element 62A on one of the first or second sections 55A, 55B and a receptacle 62B for the plug element 62A on the other of the first or second sections 55A, 55B. At least one line 26, 49, 60 for transmitting a medium, energy and/or data comprises a first line section which is provided in the first section 55A and a second line section which is provided in the second section 55B, wherein in particular the first line section and the second line section can be connected to one another by the plug connection 62. At least one line 49 for transmitting a medium, energy or data preferably passes through the plug element 62A and the receptacle 62B for the plug element 62A. At least one sealing element 63 is preferably provided on the interface or sectional plane between the two sections 55A, 55B and/or on the plug connection 62 and/or on the connecting region between the first line section and the second line section.

At least one of the two sections 55A, 55B of the adapter or of the coupling device 1A that can be releasably connected to one another is preferably made of plastic. The outer sleeve 61 of the adapter or of the coupling device 1A is preferably made of metal.

FIG. 4 shows a second embodiment of a medical or dental device 1B in the form of a handle element, a handpiece or contra-angle handpiece having a fluid-operated dynamoelectric converter. The device 1B comprises a head section 64 in which in particular a tool holder for a treatment tool that can be set in motion is disposed.

The fluid-operated dynamoelectric converter provided in device 1B is preferably identical to the fluid-operated dynamoelectric converter 3 described above. In particular the dynamoelectric converter 3 is disposed in a receptacle 48 in such a way that the fluid line 10 which is designed in one piece with the sleeve or the outer sleeve 9 at least protrudes at its end facing away from the dynamoelectric converter 3 beyond the connecting end 2A of the device 1B. The fluid line 10 is thus releasably connectable in particular directly to a fluid line, preferably to a fluid line that is connected to a fluid source, for example, to a fluid line of a supply tubing. The fluid line 10 which is designed in one piece with the sleeve or outer sleeve 9 thus preferably forms at least a part of the coupling unit 65 on the connecting end 2A for connection to a fluid source and/or a coupling element for connection to a fluid source. Optionally at least one additional line 66 for transfer of a fluid is provided on the coupling unit 65, in particular in the form of a tube which protrudes away from the connecting end 2A.

Alternatively, the fluid-operated dynamoelectric converter 3' provided in the device 1B does not have a fluid line 10 (see FIG. 4). In this case a fluid line 67 is formed which is provided in the device 1B and/or attached to the device 1B, supplying fluid to the generator 3', in particular to its impeller 5. The fluid line 67 is preferably provided on the connecting end 2A and protrudes in particular beyond the connecting end 2A. At least one section of the fluid line 67 is thus preferably provided on the coupling unit 65 or forms a part of the coupling unit 65. The coupling unit 65 according to FIG. 4 is designed as a plug coupling, but alternatively and in particular when providing a generator 3' without a fluid coupling 10 it may also be designed as a rotary or swivel coupling with a receptacle for a coupling journal of a coupling counterpart.

The receptacle 48 is preferably designed for conducting the fluid driving the impeller 5. The receptacle 48 and the sleeve or the outer sleeve 9 of the generator 3' are in particular disposed in such a way that a distance or a gap is formed between them in which the fluid can flow, optionally the fluid flowing to the impeller 5 and/or the fluid flowing away from the impeller 5. A fluid line 49, which is designed to receive the fluid that has passed the impeller 5 is connected to the receptacle 48 and/or arranged adjacently to the receptacle 48. The fluid line 49 is preferably connected to a fluid-operated drive device for the treatment tool, in particular to an impeller, and/or to an opening to dispense the fluid to the treatment site.

The medical or dental device 1B preferably comprises an illuminating device, in particular at least one optical semiconductor element or at least one light-emitting diode which is electrically connected to the generator 3' and/or can be supplied with electricity generated by the generator 3'. The lighting device is provided in particular in or on or adjacent to the head section 64. The lighting device is especially preferably disposed in the form of a ring around a tool receptacle opening on the head section. The lighting device is especially preferably provided with at least one opening to dispense a fluid onto the treatment site.

The invention is not limited to the embodiments presented here but instead comprises all embodiments which apply or contain the basic logical function principle of the invention. In addition, all the features of all the embodiments described and illustrated here can be combined with one another.

What is claimed is:

1. A medical or dental device which has a supply side connecting end that can be releasably connected to a fluid source and a fluid-operated dynamoelectric converter, wherein the fluid-operated dynamoelectric converter comprises:
    a rotor having an impeller that can be put into rotation by a fluid and at least one magnetic element which is connected to the impeller, so that the magnetic element can be put into rotation by the rotatable impeller,
    a stator having an electric winding which cooperates with the rotatable magnetic element, so that electricity can be generated in the electric winding,
    a sleeve, which surrounds at least parts of the rotor and/or of the stator, and
    a fluid line which is formed as one piece with the sleeve and comprises an end, wherein at least the end of the fluid line protrudes beyond the supply side connecting end of the medical or dental device.

2. The medical or dental device according to claim 1, wherein the outside of the sleeve comprises at least one groove, wherein said groove is fluidly fluidically connected to the fluid line so that a fluid that can be conducted in the fluid line and through the groove.

3. The medical or dental device according to claim 2, wherein at least one inlet opening is provided on an outside of the sleeve so that the fluid can be conducted from the groove through the at least one inlet opening into an interior of the sleeve and towards the impeller.

4. The medical or dental device according to claim 1, wherein the sleeve is elongated and comprises a connecting end on which the fluid line is provided and a receiving end having an opening through which the rotor and the electric winding of the stator can be inserted into the sleeve.

5. The medical or dental device according to claim 1, wherein a bearing site for rotatably supporting at least one of the rotor and the impeller is arranged in one of an interior of a rotor sleeve which accommodates the at east one magnetic element of the rotor and in an interior of the impeller.

6. The medical or dental device according to claim 1, wherein the electric winding of the stator comprises a printed conductor.

7. The medical or dental device according to claim 1, wherein the medical or dental device comprises a receptacle for the dynamoelectric converter on the supply side connecting end, the receptacle being shaped to accommodate at least a portion of the dynamoelectric converter when the dynamoelectric converter is installed in an operating position with at least the end of the fluid line protruding beyond the supply side connecting end.

8. A fluid-operated dynamoelectric converter, comprising:
    a rotor having an impeller that is rotatable by a fluid, the impeller having a plurality of blades and at least one magnetic element connected to the impeller and rotatable with the rotatable impeller,
    a rotor sleeve in which the at least one magnetic element of the rotor is disposed, and
    a stator with an electric winding which cooperates with the rotatable magnetic element so that electricity can be generated in the electric winding, wherein
    at least the blades of the impeller are formed as one piece with the rotor sleeve to rotate the rotor sleeve and the at least one magnetic element of the rotor disposed in the rotor sleeve.

9. The fluid-operated dynamoelectric converter according to claim 8, wherein a bearing site for rotatably supporting at least one of the rotor and the impeller is arranged in one of an interior of the rotor sleeve which accommodates the at least one magnetic element of the rotor and in an interior of the impeller.

10. The fluid-operated dynamoelectric converter according to claim 8, comprising a rotor shaft for rotatable bearing support of the rotor sleeve, wherein the rotor shaft is accommodated in at least one of an interior of the rotor sleeve and the interior of the impeller.

11. The fluid-operated dynamoelectric converter according to claim 10, wherein the rotor shaft is supported in a bearing surface that is provided outside of at least one of the rotor sleeve and the impeller.

12. The fluid-operated dynamoelectric converter according to claim 8, comprising a rotor journal which is formed as one piece with the rotor sleeve for rotatable bearing support of the rotor sleeve.

13. The fluid-operated dynamoelectric converter according to claim 8, wherein the rotor sleeve comprises a first section in which at least a part of the at least one magnetic element is accommodated and a second section on which the blades of the impeller are located, wherein the outside diameter of the first section is smaller than the outside diameter of the second section, so that a setback is formed on the first section.

14. A medical or dental device, comprising a fluid-operated dynamoelectric converter according to claim 8.

15. A fluid-operated dynamoelectric converter, comprising:
    a rotor having an impeller rotatable by a fluid and at least one magnetic element which is connected to the impeller so that the magnetic element is rotatable with the rotatable impeller,
    a stator having an electric winding which cooperates with the rotatable magnetic element, so that electricity can be generated in the electric winding, and a magnetic yoke element for concentrating and guiding the magnetic field lines of the at least one magnetic element through the electric winding, wherein
    the magnetic yoke element comprises a one-piece, sleeve-shaped magnetic yoke element which surrounds the rotor and the electric winding and comprises a magnetically conductive material.

16. The fluid-operated dynamoelectric converter according to claim 15, wherein the one-piece, sleeve-shaped magnetic yoke element comprises a receiving end on which an opening is provided through which the rotor and the electric winding of the stator can be inserted.

17. The fluid-operated dynamoelectric converter according to claim 16, wherein the opening on the receiving end of the one-piece, sleeve-shaped magnetic yoke element is releasably closed by a closure element.

18. The fluid-operated dynamoelectric converter according to claim 15, wherein the one-piece, sleeve-shaped magnetic yoke element is part of an outer sleeve formed in one piece for the dynamoelectric converter.

19. The fluid-operated dynamoelectric converter according to claim 15, wherein the electric winding of the stator comprises a printed conductor.

20. A medical or dental device, comprising a fluid-operated dynamoelectric converter according to claim 15.

* * * * *

UNITED STATES PATENT AND TRADEMARK OFFICE
CERTIFICATE OF CORRECTION

PATENT NO. : 9,670,896 B2
APPLICATION NO. : 14/199910
DATED : June 6, 2017
INVENTOR(S) : Manfred Hofbauer et al.

It is certified that error appears in the above-identified patent and that said Letters Patent is hereby corrected as shown below:

In the Claims

Column 15, Line 41, Claim 2 "fluidly fluidically" should read --fluidically--.

Column 15, Line 57, Claim 5 "the at east" should read --the at least--.

Signed and Sealed this
Nineteenth Day of March, 2019

Andrei Iancu
*Director of the United States Patent and Trademark Office*